United States Patent [19]

Uffenheimer

[11] Patent Number: 4,683,212

[45] Date of Patent: Jul. 28, 1987

[54] RANDOM ACCESS SINGLE CHANNEL SHEATH STREAM APPARATUS

[75] Inventor: Kenneth F. Uffenheimer, Mahopac, N.Y.

[73] Assignee: Technicon Instruments Corporation, Tarrytown, N.Y.

[21] Appl. No.: 431,639

[22] Filed: Sep. 30, 1982

[51] Int. Cl.$^4$ .......................................... G01N 21/05
[52] U.S. Cl. ................... 436/52; 73/863.01; 73/863.03; 137/571; 356/73; 422/81
[58] Field of Search ............................. 436/50, 52–55; 422/55, 63, 81, 82; 73/863.01, 863.03, 863.83, 864.12, 864.21, 864.22, 864.81; 137/2, 3, 10, 93, 571; 356/246, 39, 72, 73; 417/244

[56] References Cited

U.S. PATENT DOCUMENTS

| | | | |
|---|---|---|---|
| 3,800,984 | 4/1974 | Phelan | 422/100 |
| 3,802,782 | 4/1974 | Natelson | 422/65 X |
| 3,881,872 | 5/1975 | Naono | 422/81 |
| 3,925,018 | 12/1975 | Saunders | 436/165 |
| 3,989,381 | 11/1976 | Fulwyer | 356/39 |
| 4,155,978 | 5/1979 | Naono et al. | 422/64 |
| 4,207,074 | 6/1980 | Suzuki | 422/81 X |
| 4,231,990 | 11/1980 | Jottier | 422/100 |
| 4,248,293 | 2/1981 | Kamezaki et al. | 417/244 |
| 4,333,356 | 6/1982 | Bartels et al. | 422/81 |
| 4,499,053 | 2/1985 | Jones | 422/81 X |

OTHER PUBLICATIONS

Automatic Analyzer for Multi-item Clinical Test, Yoshida et al, Hitachi Review vol. 26 (1977), No. 4, pp. 145–150.

*Primary Examiner*—Barry S. Richman
*Assistant Examiner*—Michael S. Gzybowski
*Attorney, Agent, or Firm*—Jeffrey M. Greenman; James J. Romano, Jr.

[57] ABSTRACT

An apparatus and method are provided for the precisely controlled and coordinated, concomitant supply at optimal flow rates, by differential pumping, of selected sample and sheath liquids from respective pluralities of different sources thereof, to the same sheath stream flow cell for successive different types of sample analyses, thereby maximizing sample analysis accuracy and reproducibility, and reducing apparatus complexity and costs. The apparatus and method are particularly useful in high-speed automated biomedical analytical systems.

16 Claims, 2 Drawing Figures

RANDOM ACCESS SINGLE CHANNEL SHEATH STREAM APPARATUS

BACKGROUND OF THE INVENTION

1. Field of the Invention

This invention relates to the field of apparatus and method for the precisely controlled and coordinated supply of sheath stream and sample fluids to sheath stream flow cell systems, such as high-speed automated biomedical analytical systems.

2. Description of the Prior Art

Although apparatus and methods are known for the supply of sheath stream and sample fluids to sheath stream flow cells, none accomplish these functions in a precisely controlled and coordinated manner using the same sheath stream flow cell, and associated detecting and pumping means, for successive different types of sample analyses.

In many instances in the prior art peristaltic pumping is used to supply the sample fluid stream to the flow cell. This is disclosed, for example, in U.S. Pat. No. 3,740,143, wherein multi-channel peristaltic pumping is used to supply respective series of diluted blood samples to a plurality of sheath stream flow cells for a different type of sample analysis with respect to each. This leads to less than optimal accuracy in cell analyses due to marginal variations in peristaltic pump roller and pump tube dimensions, which cause variations in the diameter, velocity and/or volume of the sample fluid stream through the flow cell. Since separate pumping systems are used, with the sheath stream fluid being pressure pumped from a constantly pressurized source, variations in the essential sheath-sample fluid streams flow and volume ratios can also occur to further degrade sample analysis accuracy. In addition, peristaltic pumping requires frequent and precise calibration; while the relatively long lengths of peristaltic pump and supply tubing markedly increase the potential for sample carryover. Carryover is defined as the contamination of a succeeding sample by the residue of a preceding sample resulting in loss of accuracy. Further, peristaltic pumping, which operates by the occlusion or squeezing of the pump tubes by the pump rollers, can and does result in damage to the integrity of cells or like sample fluid particles to further degrade accuracy. Too, the requirement for separate sheath stream flow cell and associated optical and electronic detecting means, and a separate sample pumping channel, for each different type of sample analyses to be performed, add very significantly to overall complexity and cost of such analytical system.

Although more current efforts have been made to remedy some of the above-described problems through utilization of separate, finely calibrated peristaltic pumps for each of the sheath stream and sample fluids as described, for example, in paper *HYDRODYNAMICS OF CONCENTRIC PERISTALTIC LAMINAR FLOW OF TWO DIFFERENT FLUIDS* by K. Uffenheimer and I. Beretsky, M.D., presented at the Mar. 23, 1973 meeting of The American Association For Medical Instrumentation at Chicago, Ill., these efforts have not proven fully satisfactory, especially in increasingly sophisticated automated biomedical analytical systems. Again, separate sheath stream flow cell and associated detecting and pumping means are contemplated for each different type of sample analysis to be performed.

Other apparatus and methods are known for the supply of sheath stream and sample fluids to a sheath stream flow cell and, as disclosed in U.S. Pat. No. 3,661,460, use a combination of gravity feed, peristaltic pumping and vacuum pumping, requiring liquid trap, pressure regulation, pressure gauge, and needle valve or other flow restrictor means, to those ends. These apparatus and methods can be difficult to calibrate and tend not to remain calibrated, and thus have also not proven fully satisfactory, especially in increasingly sophisticated automated biomedical analytical systems. Again, a separate sheath stream flow cell, and associated detecting and pumping means, are required for each type of sample analysis to be performed.

Apparatus and method for the precisely controlled and coordinated supply of sample and sheath stream fluids under optimal conditions to maximize the accuracy and reproducibility of successive sample analyses are disclosed in the copending application of Gregory A. Farrell entitled New And Improved Volumetric Pumping Apparatus And Method For Supplyinq Fluids To Sheath Stream Flow Cells, Ser. No. 408,390, filed Aug. 16, 1982, now abandoned, and assigned to the assignee hereof. There too, however, a separate sheath stream flow cell and associated detecting and pumping means is required for each different type of sample analysis to be performed.

Sheath stream flow cell analysis apparatus utilizing a selector valve to permit somewhat different types of sample analyses by the same sheath stream flow cell are known in the form of the hematology instrument "Ortho ELT8" as manufactured by Ortho Diagnostic Systems, Inc. of Westwood, Mass. However, this instrument utilizes independent and complex sample fluid supply channels, rather than separate sample fluid sources, for different sample analyses, thereby requiring at least one separate sample fluid pump for each sample fluid analysis of interest with resultant increase in the overall complexity, cost and maintenance requirements of the apparatus. This also increases sample carryover. Too, no provision is made in this apparatus for the selection and supply of different sheath stream fluids to the flow cell whereby successive markedly different types of sample analyses, requiring in turn markedly different types of respectively optically compatible sheath stream fluids, cannot be performed thereon. Also, no provision is made in this apparatus for the precisely coordinated and controlled differential pumping of the sample and sheath fluids to the flow cell, thus rendering extremely difficult, if not impossible, the true optimization of the accuracy and reproducibility of the sample analysis results.

OBJECTS OF THE INVENTION

It is, accordingly, an object of the present invention to provide a random access single channel sheath stream apparatus and method for the precisely controlled and coordinated supply of sheath stream and sample fluids from respective pluralities of different sources thereof to a common sheath stream flow cell for sample fluid analyses, thereby optimizing the accuracy and reproducibility of those analyses results.

Another object of this invention is the provision of an apparatus and method for the sequential supply of reproducible volumes of corresponding portions of each of a series of samples along with a precisely coordinated volume of an optically compatible sheath stream fluid in each instance, to the same sheath stream flow cell under constant, optimal sample and sheath stream diameter, velocity and volume flow conditions, in respect of each corresponding sample portion.

Another object of this invention is the provision of an apparatus and method which are particularly adapted for different types of differentiation and counting of sample particles through use of the same sheath stream flow cell, and associated detecting and pumping means, thereby materially reducing apparatus cost and complexity.

Another object of the invention is the provision of apparatus and method which are operable with minimal, if any, damage to the sample particles.

Another object of this invention is the provision of an apparatus and method which substantially reduce sample carryover wherein successive samples are supplied, in turn, to the sheath stream flow cell for sequential sample analyses.

Another object of this invention is the provision of an apparatus and method with minimal calibration requirements and maximal calibration retention.

Another object of this invention is the provision of an apparatus and method which are operable at extremely high sample analyses rates.

Another object of this invention is the provision of apparatus and method which are particularly versatile in operation and which can be very readily adapted for use with wide ranges of different sample and sheath stream liquids attendant the performance of a wide variety of different analyses on the sample liquids.

SUMMARY OF THE INVENTION

A random access single channel sheath stream apparatus and method for supplying sample and sheath liquids to a sheath stream flow cell for successive, different types of sample analyses are disclosed, and comprise a plurality of separate sources of differently reacted sample liquid portions, and a plurality of separate sources of different, respectively optically compatible sheath liquids. Variable speed sample and sheath liquid pumps are connectable to selected ones of said sample and sheath liquid sources by flow directing and control means, and are operable to differentially pump, by concomitantly pumping and aspirating, the selected sample and sheath liquids through a single channel, e.g. common flow cell at optimal, precisely coordinated flow rates to maximize the accuracy and reproducibility of the sample analyses results in each instance. A shuttle pump is provided to rapidly prime the sample liquid pump and thereby increase the operational speed of the apparatus. The use of the same sheath stream flow cell for different types of sample analyses significantly reduces the complexity and cost of the apparatus. The apparatus find particularly useful application in high-speed, automated biomedical analytical systems.

DESCRIPTION OF A PREFERRED EMBODIMENT

Figure 1A:
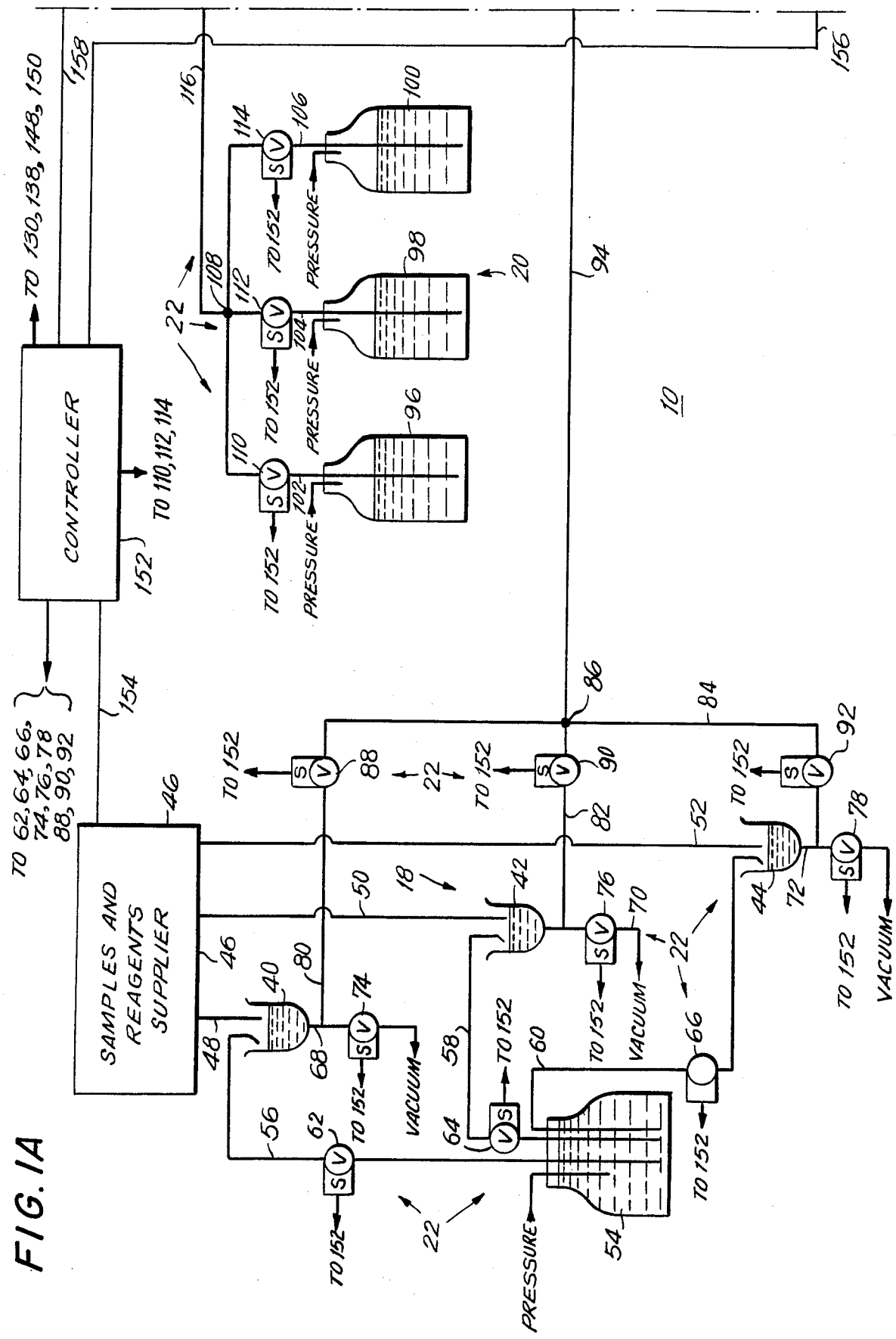
FIGS. 1A and 1B are generally schematic diagrams of the apparatus of the invention, depicted with a sheath stream flow cell.
Figure 1B:
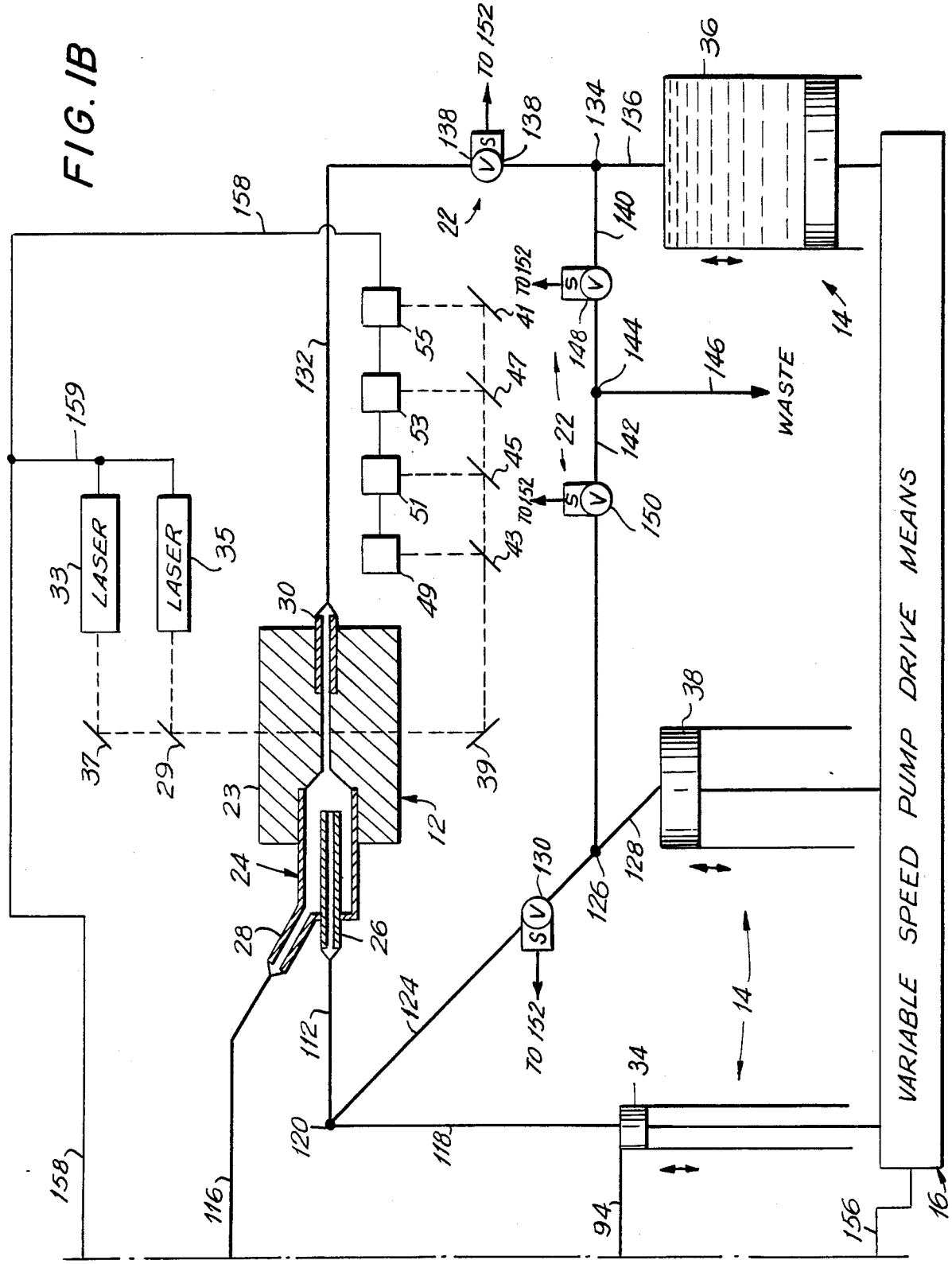

Referring now to FIGS. 1A and 1B, the random access single channel sheath stream apparatus 10 of the invention is shown with a sheath stream flow cell 12. Apparatus 10 comprise pump means 14 which supply selected sheath and sample fluids for concomitant flow through flow cell 12 for sample fluid analysis. Variable speed pump drive means are indicated. schematically at 16. Plural sample and sheath fluid sources are indicated generally at 18 and 20, respectively. Flow directing and control means 22 comprise a plurality of solenoid or other valve-controlled conduits which operate to select sample and optically compatible sheath fluids from the respective plural sources thereof for concomitant flow through flow cell 12 as directed by an apparatus controller 152.

Sheath stream flow cell 12 may, for example, generally take the form of that disclosed in U.S. Pat. No. 3,661,460, cited above, the disclosure of which is incorporated by reference herein. Flow cell 12 comprises a body 23 and concentric flow module 24 with the latter including a sample stream inlet 26, sheath stream inlet 28, and a mixed stream outlet 30. Although not, per se, forming part of this invention, it may be understood that the sheath stream flow cell 12 brings the sample and sheath streams introduced at inlets 26 and 28, respectively, together to form a pair of concentric, substantially unmixed streams, with the sample stream at the center. Detecting and counting means 32 comprises lasers 33 and 35 of different wavelengths, mirrors 37, 39 and 41, dichroic mirrors 29, 43, 45 and 47, and detectors 49, 51, 53 and 55, operatively arranged relative to flow cell 12. The detecting and counting means 32 is operative to count and size particles per unit volume of the sample stream as the ensheathed stream flows through the flow cell body 23. Precise control of the velocity, stability and diameter of the sample stream provide for a precise counting and sizing process.

Pump means 14 comprises sample fluid pump 34, sheath fluid pump 36, and shuttle pump 38; each of which is preferably a syringe pump of the type manufactured by the Hamilton Company of Reno, Nev. Such pumps are calibratable and traceable to the particularly demanding standards of the National Bureau of Standards and, once satisfactorily calibrated, tend to remain so for long periods of operational time. Pump drive means 16 preferably take the form of precisely controlled stepping motors which may be microprocessor controlled in accordance with an oscillator-generated time base. Such components are manufactured by the Superior Electric Company of Bristol, Conn. This pump and pump drive means combination provides for precise control of the respective pump flow rates and flow volumes. Preferably, shuttle pump 38, sheath fluid pump 36 and pump drive means 16 are arranged so that pumps 38 and 36 are 180° out of phase. Thus, for example, with pump 38 at top dead center, pump 36 will be at bottom dead center and vice versa.

Sample fluid sources 18 comprise reaction vessels 40, 42 and 44, respectively. Samples and reagents supplier 46, which may take any appropriate known form supplies sample and reagent fluids to reaction vessels 40, 42 and 44 through conduits 48, 50 and 52, respectively.

Constantly pressurized wash liquid reservoir 54 supplies a wash liquid to reaction vessels 40, 42 and 44 through conduits 56, 58 and 60, respectively. Solenoid operated valves 62, 64 and 66 are respectively disposed along conduits 56, 58 and 60 and are operable to permit or prevent wash liquid flow therethrough.

Reaction vessels 40, 42 and 44 respectively include drain conduits 68, 70 and 72 extending downwardly from the vessel bottoms to vacuum; and solenoid operated valves 74, 76 and 78 are respectively disposed along drain conduits 68, 70 and 72 to permit or prevent flow therethrough. Conduits 80, 82 and 84 respectively connect drain conduits 68, 70 and 72 as shown, above the drain conduit valve in each instance, to four way junction 86; and solenoid operated valves 88, 90 and 92 are respectively disposed along conduits 80, 82 and 84 to permit or prevent flow therethrough. Conduit 94 connects junction 86 to sample pump 34 and supplies reacted sample fluids thereto.

Sheath fluid sources 20 comprise constantly pressurized sheath fluid reservoirs 96, 98 and 100, respectively. Conduits 102, 104 and 106 respectively connect the sheath fluid reservoirs 96, 98 and 100 to four way junction 108; and solenoid operated valves 110, 112 and 114 are respectively disposed along conduits 102, 104 and 106 to permit or prevent flow therethrough. A sheath fluid supply conduit 116 connects junction 108 to sheath stream inlet 28 of the sheath stream flow cell 12.

Conduit 118 connects sample pump 34 to three way junction 120, and reacted sample supply conduit 112 connects junction 120 to sample stream inlet 26 of the sheath stream flow cell 12. Conduit 124 connects junction 120 to three way junction 126, and conduit 128 connects the latter to shuttle pump 38. Solenoid operated valve 130 is disposed along conduit 124 to permit or prevent flow therethrough.

Conduit 132 connects mixed stream outlet 30 of the flow cell 12 to three way junction 134, and conduit 136 connects the latter to sheath fluid pump 36. A solenoid operated valve 138 is disposed along conduit 132 to permit or prevent flow therethrough. Conduits 140 and 142 respectively connect junctions 134 and 126 to three way junction 144, and conduit 146 connects junction 144 to waste. Solenoid operated valves 148 and 150 are respectively disposed along conduits 140 and 142 to permit or prevent flow therethrough.

Controller 152 is operable through connectors 154, 156 158 and 159 to control and coordinate the respective operations of samples and reagents supplier 46, pump drive means 16, and detecting and counting means 32. In addition, controller 152 is operable as indicated to control and coordinate the respective operations of the solenoid operated valves 62, 64, 66, 74, 76, 78, 88, 90, 92, 110, 112, 114, 130, 138, 148 and 150 of the flow directing and control means 22. Where the apparatus conduits are resilient tubing, the respective solenoid operated valves may be pinch valves.

A representative application of the apparatus and method of this invention is as a hematology instrument for the automated counting and sizing of the red blood cells and platelets, the basophils, and all of the other white blood cells except basophils, as are respectively contained in a series of diluted blood sample portions which are supplied in turn, each with an appropriate reagent quantity, to the reaction vessels 40, 42 and 44 by samples and reagents supplier 46 in timed sequence with overall apparatus operation as determined by controller 152. In such instance, sheath fluid reservoirs 96, 98 and 100 would respectively contain a sheath liquid which is optically compatible with red blood cell and platelet counting and sizing, a sheath liquid which is optically compatible with basophil counting and sizing, and a sheath liquid which is optically compatible with the counting and sizing of all other white blood cells except basophils.

For such application, appropriate quantities of the reacted sample portions of the same blood sample from reaction vessels 40, 42, and 44 along, in each instance, with an appropriate quantity of the selected, refractive index-compatible sheath liquid from one of the reservoirs 96, 98 and 100, are concomitantly pumped in turn, as directed by flow control means 22, to and through the same sheath stream flow cell 12 by pump means 14 for respective red blood cell and platelet, basophil, and remaining white blood cell counting and sizing by detecting and counting means 32, all in timed sequence as determined by controller 152. The remaining, reacted blood sample portions are then emptied from the reaction vessels 40, 42 and 44; and the reaction vessels are then washed by wash liquid from reservoir 54 to minimize sample carryover (the contamination of a succeeding sample by the residue of a preceding sample), again in timed sequence as determined by controller 152. Thereafter, portions of the next succeeding blood sample, with appropriate reagent quantities in each instance, are supplied to reaction vessels 40, 42 and 44 by samples and reagents supplier 46 for repetition of the cell counting and sizing process.

More specifically, at the beginning of an operating sequence, each of reaction vessels 40, 42 and 44 contain appropriately reacted portions of the same blood sample, pressurized sheath reservoirs 96, 98 and 100 contain appropriate quantities of refractive index-compatible sheath liquids, shuttle pump 38 and sample pump 34 are at top dead center (as shown), and sheath pump 36 is at bottom dead center and filled with preceding sample and sheath liquids (as shown). All solenoid operated valves are closed, and all conduits are liquid filled except for drain conduits 68, 70 and 72. Opening of valves 110, 150 and 138 by controller 152 will flow pressurized sheath liquid from reservoir 96 through conduit 102, junction 108, conduit 116, flow cell inlet 28, flow cell 12, flow cell outlet 30, conduit 132, junction 134, and conduits 140 and 146 to waste. This purges the flow cell of the residue of the preceding sample and sheath liquids to minimize sample and sheath liquid carryover and maximize analysis accuracy; it being well understood by those skilled in this art that sample carryover in the interior optical window of flow cell flow chamber 24 can be particularly detrimental to optical counting of low signal level sample liquid particles. Controller 152 then closes valves 110, 150 and 138.

Controller 152 then opens valves 88, 130 and 150, and the piston of shuttle pump 38 is driven down by pump drive means 16 to rapidly aspirate the segment of air which is trapped by surface tension in drain conduit 68 above valve 74, followed by the reacted sample from reaction vessel 40, through conduit 80, junction 86, conduit 94, sample pump 34, conduit 118, junction 120, conduit 124, junction 126 and conduit 128. This purges the preceding sample from the sample pump 34 and conduits 80, 94 and 118 to further minimize sample carryover, and washes in the reacted sample from vessel 40 substantially to the inlet of flow cell 12. Concomitantly, the piston of sheath fluid pump 36 is driven up by pump drive means 16 to rapidly discharge its contents of sample and sheath liquids from the preceding analyses to waste through conduit 136, junction 134, conduit 140, junction 144 and conduit 146. The piston of sample fluid pump 34 is then driven down by pump drive means 16 to aspirate reacted sample liquid from reaction vessel 40 through drain conduit 68, conduit 80, junction 86 and conduit 94. Controller 152 then closes valves 88, 130 and 150.

With the desired sample so-positioned, controller 152 opens valves 110, 148 and 138. The piston of sample fluid pump 34 is driven up by pump drive means 16 to positively pump, at a precisely controlled optimal flow rate, the pump-contained reacted sample liquid from reaction vessel 40 through the flow cell 12 through conduit 118, junction 120, conduit 122 and flow cell inlet 26. Concomitantly, the piston of sheath fluid pump 36 is driven down by pump drive means 16 to aspirate, also at precisely controlled optimal flow rate, the optically compatible sheath liquid from reservoir 96 through the flow cell 12 through conduit 102, junction 108, conduit 116, flow cell sheath inlet 28, flow cell 12, flow cell outlet 30, conduit 132, junction 134 and conduit 136. In addition, the reacted sample liquid from vessel 40, as pumped through flow cell 12 by sample fluid pump 34, is also aspirated into sheath fluid pump 36 from the flow cell outlet 30. This forms the concentric sample-sheath liquid streams through the flow cell under precisely controlled and coordinated, readily reproducible conditions of constant, and optimal, sample and sheath liquid stream diameters, velocity and flow volumes in respect to the sample liquid from reaction vessel 40. Once steady state sheath stream flow conditions through flow cell 12 are reached, controller 152 activates the appropriate one of lasers 33 and 35, and the appropriate one of detectors 49, 51, 53 and 55 (both in accordance with the particular characteristics of the sample analysis of interest) for a precisely predetermined time period of cell counting and sizing operation; which time period is the same for all sample liquids from reaction vessel 40.

With sheath fluid pump 36, sample fluid pump 34, and the respective sheath liquid reservoirs 96, 98 and 100 configured and operatively connected as described through the sheath stream flow cell 12, it will be clear that a precisely operable and coordinated differential pumping arrangement is provided. More specifically, with incompressible fluids, the flow rate at which the sheath liquid is aspirated as described by sheath fluid pump 36 will be precisely equal to the difference between the total flow rate into sheath fluid pump 36 and the flow rate at which the sample liquid is pumped as described from sample fluid pump 34. This insures that the flow rate of the sheath liquid through the sheath stream flow cell 12 will be precisely equal to the difference between the total flow rate through the flow cell and the flow rate of the sample liquid therethrough. Thus, with a constant and precisely determinable total flow rate into sheath fluid pump 36, it will be clear that precise determination and control of the sample liquid flow rate out of sample fluid pump 34 to and through the sheath stream flow cell 12 will operate in turn to precisely determine and control the sheath liquid flow rate through the flow cell 12; whereby the essential sheath and sample liquid stream diameters, flow rates and flow velocities through the flow cell 12, and the respective ratios therebetween, may be optimized and maintained consistent for each particular type of sample analysis of interest. This maximizes the accuracy and reproducibility of the sample analysis results.

Simultaneously with cell counting and sizing, the piston of shuttle pump 38 is driven up by drive means 16 to discharge its contents of the reacted sample liquid from reaction vessel 40 through conduit 128, junction 126, conduit 142, junction 144 and conduit 146 to waste. Controller 152 then closes valves 110, 148 and 138.

To begin analysis of the reacted sample portion from reaction vessel 42, controller 152 opens valves 112, 150 and 138 allowing sheath liquid from reservoir 98 to purge flow cell 12 by flowing through conduit 104, junction 108, conduit 116, flow cell inlet 28, flow cell 12, flow cell outlet 30, conduit 132, junction 134, conduit 140, junction 144 and conduit 146 to waste. Controller 152 then closes valves 112, 150 and 138.

Valves 90, 130 and 150 are then opened by controller 152, and the piston of shuttle pump 38 driven down by drive means 16 to rapidly aspirate the segment of air drain conduit 70 followed by the reacted sample liquid from reaction vessel 42 through conduit 82, junction 86, conduit 94, sample fluid pump 34, conduit 118, junction 120, conduit 124, junction 126 and conduit 128. This purges the residue of the preceding sample from reaction vessel 42 from conduit 82, and purges the residue of the preceding sample from reaction vessel 40 from junction 86, conduit 94, pump 34, conduit 118, junction 120 and conduit 124, all to further minimize sample carryover. This also washes in the reacted sample liquid from reaction vessel 42 substantially to flow cell sample inlet 26. Concomitantly, the piston of sheath fluid pump 36 is driven up by pump drive means 16 to rapidly discharge its contents of sample and sheath liquids from the preceding analysis of the reacted sample liquid from reaction vessel 40 through conduit 136, junction 134, conduit 140, junction 144 and conduit 146 to waste.

The piston of sample pump 34 is then driven down by pump drive means 16 to aspirate reacted sample liquid from reaction vessel 42 through drain conduit 70, conduit 82, junction 86 and conduit 94. Controller 152 then closes valves 90, 130 and 150. With the desired sample so positioned, controller 152 opens valves 112, 148 and 138. Sample pump 34 is then driven up by pump drive means 16 to positively pump, at a precisely controlled optimal flow rate, the pump-contained reacted sample liquid from reaction vessel 42 through flow cell 12 through conduit 118, junction 120, conduit 122 and the flow cell inlet 12. Concomitantly, the piston of sheath fluid pump 36 is driven down by pump drive means 16 to aspirate, also at a precisely controlled optimal flow rate, the optically compatible sheath liquid from reservoir 98 through conduit 104, junction 108, conduit 116, flow cell sheath inlet 28, flow cell 12, flow cell outlet 30, conduit 132, junction 134 and conduit 136. In addition, the reacted sample liquid from vessel 42 as pumped through the flow cell 12 by sample fluid pump 34 is also aspirated into sheath fluid pump 36 from flow cell outlet 30. This forms the concentric, sample-sheath liquid streams through flow cell 12 under precisely controlled and coordinated, readily reproducible conditions of constant, and optimal, sample and sheath liquid stream diameters, velocity and flow volumes in respect to the reacted sample liquid from reaction vessel 42. As with the previous sample, once steady state sheath stream flow conditions through flow cell 12 are reached, controller 152 activates the appropriate ones of the lasers 33 and 35, and the detectors 49, 51, 53 and 55, respectively, for a precisely predetermined timed period of cell counting and sizing operation which is the same for all reacted sample liquids from reaction vessel 42.

Simultaneously with this cell counting and sizing, the piston of shuttle pump 38 is again driven by drive means 16 to discharge its contents of the reacted sample liquid from reaction vessel 42 through conduit 128, junction 126, conduit 142, junction 144 and conduit 146 to waste. Controller 152 then closes valves 112, 148 and 138.

To begin analysis of the reacted sample liquid portion from reaction vessel 44, controller 152 opens valves 114, 150 and 138 allowing sheath liquid from reservoir 100 to purge flow cell 12 as previously described, whereupon controller 152 closes those valves. Next, controller 152 opens valves 92, 130 and 150, and the piston of shuttle pump 38 is driven down by pump drive means 16 to rapidly aspirate the segment of air from drain conduit 72 followed, by reacted sample liquid from reaction vessel 44, through drain conduit 72, conduit 84, junction 86, conduit 94, sample fluid pump 34, conduit 118, junction 120, conduit 124, junction 126 and conduit 128. This purges the preceding sample residue from sample pump 34 and the relevant conduits and junctions, and washes in the reacted sample liquid from reaction vessel 44 substantially to the flow cell inlet 26. Concomitantly, the piston of sheath fluid pump 36 is driven up by pump drive means 16 to rapidly discharge its contents of sample and sheath liquids from the preceding analysis to waste as described above.

The piston of sample pump 34 is then driven down by pump drive means 16 to aspirate reacted sample liquid from reaction vessel 44 through drain conduit 72, conduit 84, junction 86 and conduit 94. Controller 152 then closes valves 92, 130 and 150. With the desired sample so-positioned, controller 152 opens valves 114, 148 and 138. The piston of sample fluid pump 34 is then driven up by pump drive means 16 to positively pump, at a precisely controlled optimal flow rate, the pump-contained reacted sample liquid from reaction vessel 44 to and through the flow cell inlet 26. Concomitantly, the piston of sheath fluid pump 36 is driven down by pump drive means 16 to aspirate, also at precisely controlled optimal flow rate, the optically compatible sheath liquid from reservoir 100 to and through the flow cell 12 through conduit 106, junction 108, conduit 116, flow cell sheath inlet 28, flow cell 12, flow cell outlet 30, conduit 132, junction 134 and conduit 136. In addition, the reacted sample liquid from vessel 44, as pumped through flow cell 12 by sample fluid pump 34, is also aspirated into sheath fluid pump 36 from flow cell outlet 30. This forms the concentric sample-sheath liquid streams through flow cell 12 under precisely controlled and coordinated, readily reproducible conditions of constant, and optimal, sample and sheath liquid stream diameters, velocity and flow volumes in respect to the reacted sample liquid from reaction vessel 44. Again, once steady state sheath stream flow conditions are reached in sheath stream flow cell 12, controller 152 activates detecting and counting means 32 for a precisely predetermined time period of cell counting and sizing operation. This time period is the same for all reacted sample liquids from reaction vessel 44.

Simultaneously with this cell counting and sizing, the piston of shuttle pump 38 is again driven up by pump drive means 16 to discharge its contents of the reacted sample liquid from reaction vessel 44 to waste as previously described. Controller 152 then closes valves 112, 148 and 138 to prepare the apparatus 10 for the next cycle of operation as described.

The time sequence of the supply of the samples and reagents to the respective reaction vessels 40, 42 and 44 by supplier 46 is selected to avoid loss in operational time and thus maximize the sample analysis rate of apparatus 10. As soon as valve 88 is closed by controller 152 following aspiration of reacted sample liquid from reaction vessel 40, the controller opens valve 74 to drain the remainder of the reacted sample liquid in reaction vessel 40 under vacuum through drain conduit 68 to waste. Once this is completed, controller 152 opens valve 62 to supply wash liquid from wash liquid reservoir 54 to reaction vessel 40 to rapidly wash the residue of the reacted sample liquid therefrom for drain, under vacuum through drain conduit 68 to waste. Valve 62 is then closed by controller 152 whereby, with valve 74 remaining open, ambient air will be drawn to vacuum through the reaction vessel 40 and drain conduit 68 to further, and rapidly, remove reacted sample and wash liquid residues therefrom and dry the vessel. Valve 74 is then closed by controller 152, and samples and reagents supplier 46 activated by the latter to supply an appropriate portion of the succeeding sample, along with an appropriate reagent quantity, to reaction vessel 40 through conduit 48 for commencement of the desired reaction. Thus, no operational time of the apparatus 10 is lost in waiting for this reaction which may proceed to completion during the analysis as described of the preceding reacted sample liquid from reaction vessel 40 or, if more time consuming, certainly during the analyses of the reacted sample liquids from reaction vessels 42 and 44. This overlapping of the sample liquid-reagent reaction and sample liquid analyses times operates to provide a higher operational rate for the apparatus 10 than would otherwise be possible in that an appropriately reacted sample liquid is always immediately available for analysis.

Operation of pressurized wash liquid reservoir 54 and samples and reagents supplier 46 vis-a-vis reaction vessels 42 and 44 through conduits 58, 60, 50 and 52, valves 76 and 78, and drain conduits 70 and 72 is the same as described for reaction vessel 40.

Additional increase in the overall operational rate of apparatus 10 is provided by variable speed pump drive means 16 which enable the rapid washing in or priming of the apparatus, and the rapid establishment of a steady state sample stream by the shuttle pump 38, and the rapid initial achievement of steady state sample and sheath liquid streams thrgugh sheath stream flow cell 12 by sample and sheath fluid pumps 34 and 38; all followed as required by coordinated reduction in sample and sheath fluid pump drive rates to assure optimal stream flow rates through flow cell 12 for respective cell counting and sizing of reacted sample liquids by detecting and counting means 32 from each of reaction vessels 40, 42 and 44. Too, shuttle pump 38 enables the rapid washing in of samples from relatively remote sample locations without sample carryover of significance thus, for example, enabling wide spacing, if desired, between the reaction vessels and the detecting and counting means.

Operation of the apparatus 10 is continuous until all of the samples in the sample series of interest have been analyzed.

Although described as comprising three reaction vessels and three sheath liquid reservoirs, the apparatus 10 is by no means limited to that number.

Various changes may be made in the disclosed preferred embodiment without departing from the scope of this invention as defined by the claims.

What is claimed is:

1. A method comprising, the steps of, selecting a sample fluid source from a plurality of separate sources of different sample fluids, selecting a source of a sheath fluid which is optically compatible with the sample fluid from the thusly selected sample fluid source from a plurality of separate sources of different sheath fluids which are respectively optically compatible with different ones of said different sample fluids, connecting the selected one, only, of said plurality of different sample fluid sources to sheath stream flow cell analysis means which includes a single sheath flow cell, concomitantly connecting the selected one, only, of said plurality of different sheath fluid sources to said sheath stream flow cell, both connecting steps performed under the control of control means operatively associated with each of said different sample and sheath stream fluid sources and said sheath stream flow cell, and concomitantly flowing the thusly selected optically compatible sample and sheath fluids through said sheath stream flow cell for sample fluid analysis by concomitantly differentially pumping the same from the respective sources thereof through said sheath stream flow cell.

2. In a method as in claim 1 wherein, the differential pumping of the selected ones of said sample and sheath fluids comprises, the steps of, pumping the selected one of said sample fluids to said sheath stream flow cell at a first flow rate, and concomitantly aspirating the selected ones of said sample and sheath fluids through said sheath stream flow cell at a second, and greater flow rate whereby, the flow rate of said sheath fluid through said sheath stream flow cell will be equal to the difference between said second and first flow rates, respectively.

3. In a method as in claim 2 further comprising, the steps of, supplying a wash liquid to the thusly selected sample fluid source following the pumping of the sample fluid therefrom whereby, the residue of said sample fluid will be washed from said sample fluid source to minimize sample fluid carryover upon repeated operation of said apparatus to sucessively select and supply sample fluids and optically compatible sheath fluids to said sheath stream flow cell.

4. In a method as in claim 2 further comprising, the steps of, flowing the thusly selected one of said sheath fluids through said sheath stream flow cell prior to the apsiration thereof with the selected one of said sample fluids therethrough whereby, said sheath stream flow cell will be purged of the residue of previous sample fluids to minimize sample fluid carryover upon repeated operation of the method to successively select and supply sample fluids and optically compatible sheath fluids to said sheath stream flow cell.

5. In a method as in claim 2 further comprising, the steps of, successively selecting and supplying different sample fluids and optically compatible sheath stream fluids to said sheath stream flow cell, and detecting respectively different characteristics of said different sample fluids for sample fluids analyses by sheath stream flow cell analysis means in accordance with said different sample fluid characteristics whereby, said different sample fluids may be analyzed with respect to different characteristics thereof through use of the same sheath stream flow cell.

6. In a method as in claim 2 wherein the selected sample fluid is pumped to said sheath stream flow cell by a sample fluid pump, and wherein said method further comprises, the steps of, pumping the selected sample fluid to and through said sample fluid pump prior to the pumping by the same of said selected sample fluid to said sheath stream flow cell whereby, said sample fluid pump will be purged of the residue of previous sample fluids to minimize sample fluid carryover upon repeated operation of the method to successively select and supply sample fluids and optically compatible sheath fluids to said sheath stream flow cell.

7. In a method as in claim 6 further comprising, the steps of, pumping a quantity of ambient air to and through said sample fluid pump prior to the pumping of the selected sample fluid to and through the same whereby, said sample fluid pump will be purged of the residue of previous sample fluids to minimize sample fluid carryover upon repeated operation of the method to successively select and supply sample fluids and optically compatible sheath fluids to said sheath stream flow cell.

8. Apparatus comprising, a plurality of separate sources of different sample fluids, a plurality of separate sources of different sheath fluids which are respectively optically compatible with different ones of said different sample fluids, sheath stream flow cell analysis means which include a sheath stream flow cell, means for selecting one of said sample fluid sources, means for selecting sheath fluid source which is optically compatible with the sample fluid from the thusly selected sample fluid source, and means for concomitantly supplying of the thusly selected optically compatible sample and sheath fluids to said sheath stream flow cell, said selection and supply means comprising, flow directing and control means operatively associated with each of said sample and sheath fluid sources, and said sheath stream flow cell, respectively, said flow directing and control means being operable to connect selected ones, only, of said sample and sheath fluid sources, and said sheath stream flow cell, for concomitant flow of said selected optically compatible sample and sheath fluids through said sheath stream flow cell for sample fluid analysis, said apparatus further comprising, pump means operatively connected to said flow directing and control means and to said sheath stream flow cell and operable to concomitantly pump the selected ones of said sample and sheath fluids from respective pump and sheath fluid sources to said sheath stream flow cell for concomitant sample and sheath fluid flow therethrough, said pump means comprising differential pump means operatively connected to inlet and outlet means respectively, of said sheath stream flow cell, said differential pump means being operable to pump the selected one of said sample fluids to said sheath stream flow cell inlet means at a first flow rate, and to concomitantly aspirate the selected ones of said sample and sheath fluids through said sheath stream stream flow cell outlet means at a second, and greater flow rate whereby, the flow rate of said sample fluid through said sheath stream flow cell will be equal to the difference between said second and first flow rates, respectively.

9. In apparatus as in claim 8 wherein, said sample fluids comprise a plurality of sample liquids, and said sheath fluids comprise a plurality of respectively optically compatible sheath liquids, and wherein said differential pump means comprise a sample liquid pump which is connectable by said flow directing and control means to the selected one of the plurality of sample liquid sources and to the sheath stream flow cell inlet means to pump the selected sample liquid from said sample liquid source to the sheath stream flow cell inlet means, and a sheath liquid pump which is connectable by said flow directing and control means through the sheath stream flow cell outlet and inlet means, respectively, to the selected one of the plurality of sheath liquid sources to concomitantly aspirate the selected sheath liquid, and the selected sample liquid as pumped by the sample liquid pump, through said sheath stream flow cell.

10. In apparatus as in claim 9 wherein, said sample liquid pump and said sheath liquid pump are respectively positive displacement pumps.

11. In apparatus as in claim 9 further comprising means to pressurize the respective sources of said sheath liquids.

12. In apparatus as in claim 9 wherein, said flow directing and control means comprise conduit means connecting said pluralities of sample and sheath liquid sources, the inlet and outlet means of said sheath stream flow cell, and said sample and sheath liquid pumps, respectively, and valve means operatively associated with said conduit means and operable to control the respective flows of said sample and sheath liquids therethrough for selection of said sample and sheath liquids.

13. In apparatus as in claim 9 further comprising, variable speed pump drive means operatively connected to said sample and sheath liquid pumps and operable to drive the same at selected pumping rates in accordance with sample and sheath liquid selection whereby, the selected sample and sheath liquids may be concomitantly pumped through said sheath stream flow cell at respectively optimal flow rates.

14. In apparatus as in claim 9 wherein, said pump means further comprise shuttle pump means which are connectable by said flow directing and control means through said sample liquid pump downstream of the latter to the selected one of said sample liquid sources, said shuttle pump means being operable to pump the selected sample liquid from said selected one of said sample liquid sources to and through said sample liquid pump prior to sample liquid-pumping operation of the latter whereby, said sample liquid pump will be purged of the residue of a previously pumped sample liquid to minimize sample liquid carryover upon repeated operation of said apparatus to successively select and supply sample liquids and optically compatible sheath liquids to said sheath stream flow cell.

15. In apparatus as in claim 9 further comprising, wash means operatively associated with said sample liquid sources and operable t supply a wash liquid thereto to wash the same following the supply of sample liquids therefrom whereby, the residues of said sample liquids will be washed from said sample liquid sources to minimize sample liquid caryover upon repeated operation of said apparatus to successively select and supply sample liquids and optically compatible sheath liquids to said sheath stream flow cell.

16. In apparatus as in claim 9 further comprising, detecting means operatively associated with said sheath stream flow cell, said detecting means being operable to detect respectively different characteristics of said different sample liquids for sample liquids analyses by said sheath stream flow cell analysis means in accordance with said different sample liquid characteristics whereby, said different sample liquids may be analyzed with respect to different characteristics thereof by said detecting means through use of the same sheath stream flow cell upon repeated operation of said apparatus to successively select and supply sample liquids and opticaly compatible sheath stream liquids to said sheath stream flow cell for analysis.

* * * * *